United States Patent
Sianturi et al.

(10) Patent No.: US 10,829,467 B2
(45) Date of Patent: Nov. 10, 2020

(54) PROCESS FOR PRODUCING A CYCLIC ACETAL IN A HETEROGENEOUS REACTION SYSTEM

(71) Applicant: Celanese Sales Germany GmbH, Sulzbach, Taunus (DE)

(72) Inventors: Joni Sianturi, Schwalbach am Taunus (DE); Hanno Hueckstaedt, Liederbach (DE); Matthias Göring, Hofheim (DE); Damian Feord, Strasbourg (FR); Stanley Leonard, Corpus Christi, TX (US)

(73) Assignee: Celanese Sales Germany GmbH, Taunus (DE)

( * ) Notice: Subject to any disclaimer, the term of this patent is extended or adjusted under 35 U.S.C. 154(b) by 0 days.

(21) Appl. No.: 16/368,141

(22) Filed: Mar. 28, 2019

(65) Prior Publication Data
US 2019/0300497 A1    Oct. 3, 2019

Related U.S. Application Data

(60) Provisional application No. 62/649,998, filed on Mar. 29, 2018.

(51) Int. Cl.
*C07D 323/06* (2006.01)
*B01J 8/02* (2006.01)
*B01D 3/00* (2006.01)

(52) U.S. Cl.
CPC ............ *C07D 323/06* (2013.01); *B01D 3/00* (2013.01); *B01J 8/02* (2013.01); *B01J 2208/00017* (2013.01); *B01J 2208/00539* (2013.01); *B01J 2208/00893* (2013.01); *B01J 2208/027* (2013.01)

(58) Field of Classification Search
CPC . C07D 323/06; B01J 8/02; B01J 2208/00539; B01J 2208/00017; B01J 2208/027; B01J 2208/00893; B01D 3/009; B01D 3/10; B01D 3/00
See application file for complete search history.

(56) References Cited

U.S. PATENT DOCUMENTS

| | | | |
|---|---|---|---|
| 2,078,534 A | 4/1937 | Groll et al. |
| 3,305,529 A | 2/1967 | Reynolds et al. |
| 3,457,227 A | 7/1969 | Kennedy |
| 3,471,998 A | 10/1969 | Ishida et al. |
| 3,506,615 A | 4/1970 | Chen |
| 3,697,546 A | 10/1972 | Asakawa et al. |
| 3,804,808 A | 4/1974 | Ishii et al. |
| 4,323,502 A | 4/1982 | Muck et al. |
| 4,330,474 A | 5/1982 | Nehring |
| 4,358,623 A | 11/1982 | Murphy et al. |
| 4,420,641 A | 12/1983 | Gerberich et al. |
| 4,450,301 A | 5/1984 | McMillan et al. |
| 4,563,536 A | 1/1986 | Yoshida et al. |
| 4,962,235 A | 10/1990 | Morishita et al. |
| 4,967,014 A | 10/1990 | Masamoto et al. |
| 5,008,463 A | 4/1991 | Beck et al. |
| 5,508,448 A | 4/1996 | Emig et al. |
| 5,767,294 A | 6/1998 | Steele et al. |
| 5,929,257 A | 7/1999 | Kashihara et al. |
| 6,232,507 B1 | 5/2001 | Kaiser et al. |
| 6,313,323 B1 | 11/2001 | Werner |
| 6,362,305 B1 | 3/2002 | Schweers et al. |
| 6,388,102 B2 | 5/2002 | Schweers et al. |
| 6,448,448 B1 | 9/2002 | Schweers et al. |
| 6,472,566 B2 | 10/2002 | Schweers et al. |
| 6,653,487 B2 | 11/2003 | Schweers et al. |
| 6,781,018 B2 | 8/2004 | Liu et al. |
| 7,153,999 B2 | 12/2006 | Watanabe |
| 7,301,055 B2 | 11/2007 | Hoffmockel et al. |
| 7,390,932 B2 | 6/2008 | Stroefer et al. |
| 7,598,402 B2 | 10/2009 | Chen et al. |
| 9,365,537 B2 | 6/2016 | Haubs et al. |
| 9,469,624 B2 | 10/2016 | Haubs |
| 9,499,512 B2 * | 11/2016 | Haubs ................ C07D 323/06 |
| 9,546,148 B2 * | 1/2017 | Haubs .................. C08G 65/16 |
| 9,574,061 B2 | 2/2017 | Haubs et al. |
| 9,604,956 B2 | 3/2017 | Haubs et al. |

(Continued)

FOREIGN PATENT DOCUMENTS

| | | |
|---|---|---|
| AT | 252913 | 3/1967 |
| CN | 101665409 | 3/2010 |
| DE | 4137846 | 5/1993 |
| DE | 19822598 | 11/1999 |
| GB | 1012372 | 12/1965 |
| GB | 1130513 | 10/1968 |
| GB | 1524440 | 9/1978 |
| WO | WO-2014017203 A1 * | 1/2014 ........... C07D 323/06 |

OTHER PUBLICATIONS

Grant & Hackh's Chemical Dictionary (5th Ed. 1987) p. 148.*

(Continued)

*Primary Examiner* — John M Mauro
(74) *Attorney, Agent, or Firm* — Dority & Manning, P.A.

(57) ABSTRACT

A process for producing a cyclic acetal is disclosed. According to the process, a formaldehyde source is combined with an aprotic compound and contacted with a heterogeneous catalyst which causes the formaldehyde source to convert into a cyclic acetal such as trioxane. The catalyst, for instance, may comprise a solid catalyst such as an ion exchange resin. In one embodiment, the process is used for converting anhydrous formaldehyde gas to trioxane. The anhydrous formaldehyde gas may be produced form an aqueous formaldehyde solution by an extractive distillation. The aprotic compound and the formaldehyde solution may be extracted from the reaction product and recycled into the process.

20 Claims, 2 Drawing Sheets

(56) References Cited

U.S. PATENT DOCUMENTS

| | | | |
|---|---|---|---|
| 2001/0053865 A1 | 12/2001 | Schweers | |
| 2006/0058537 A1 | 3/2006 | Haubs et al. | |
| 2006/0185513 A1 | 8/2006 | Stroefer et al. | |
| 2008/0234459 A1 | 9/2008 | Lang et al. | |
| 2010/0004409 A1 | 1/2010 | Schwittay et al. | |
| 2010/0121081 A1 | 5/2010 | Lang et al. | |
| 2010/0145079 A1 | 6/2010 | Stroefer et al. | |
| 2014/0343300 A1* | 11/2014 | Haubs | C08J 11/16 549/368 |
| 2014/0350216 A1* | 11/2014 | Haubs | C08G 65/30 528/403 |

OTHER PUBLICATIONS

Price, M.P. (2003); excerpt downloaded from http://facstaff.cbu.edu/rprice/lectures/flash.html01/02/2020); p. 1.*

Sorsamaki, L., VTT-R-06143-15 Research Report Design and selection of separation processes 2015; excerpt provided p. 1-4.*

WO-2014017203-A1 (2014); WIPO English Machine Translation p. 1-31.*

International Search Report and Written Opinion for application PCT/US19/24604 dated Jun. 12, 2019.

Yamaguchi T. et al: "Synthesis of cyclooligomers of formaldehyde in liquid sulfur dioxide", Chemistry and Industry, vol. 43, Oct. 23, 1971 (Oct. 23, 1971) pp. 1226-1227, XP008149518, Society of Chemical Industry, London; GB ISSN: 0009-3068.

Shoujin Su, Philippe Zaza and Albert Renken: Catalytic Dehydrogenation of Methanol to Water-Free Formaldehyde, Chem. Eng. Technol. 17 (1994) pp. 34-40.

Abstract of Japanese Patent—JPH06228126, Aug. 16, 1994, 1 page.

Abstract of Japanese Patent JP2007230979, Sep. 13, 2007, 2 pages.

JP S47-007029 B.

JP S46-031867 B.

JP S37-011033 B.

New Jersey Department of Health and Senior Services, Hazardous Substance Fact Sheet. "Boron Trifluoride Diethyl Etherate." (c) Apr. 2000. Available from : < http://nj.gov/health/eoh/rtkweb/documents/fs/0248.pdf>.

Cao et al., 2012, caplus an 2012:1246481.

Drent et al., 2001, caplus an 2001: 507659.

Chen et al., 2010, caplus an 2010: 312723.

Ionic-Liquid, 2016, https://en.wikipedia.org/wiki/Ionic_liquid.

U.S. Appl. No. 14/359,308, filed May 20, 2014.

U.S. Appl. No. 15/179,548, filed Jun. 10, 2016.

The Unit Converter, © 2011, Available from: <http://www.theunitconverter.com/torr-to-bar-conversion/760-torr-to-bar.html>., 6 pages.

* cited by examiner

PROCESS FOR PRODUCING A CYCLIC ACETAL IN A HETEROGENEOUS REACTION SYSTEM

RELATED APPLICATIONS

The present application is based upon and claims priority to U.S. Provisional Application Ser. No. 62/649,998, having a filing date of Mar. 29, 2018, which is incorporated herein by reference in its entirety.

BACKGROUND 1,3,5-Trioxane (hereinafter "trioxane") is the cyclic trimer of formaldehyde. Trioxane is mainly used as a starting material for the manufacturing of polyoxymethylenes (POM) which is a high performance polymer having desirable and exceptional properties in terms of mechanical, chemical and temperature stability. Polyoxymethylene polymers are available as homo- and copolymers.

As the polyoxymethylene market is growing, there is a desire on the side of the trioxane producers to expand their production capacities in order to satisfy the trioxane demand on a competitive basis. The major technical process for the production of trioxane is the conversion of aqueous formaldehyde solutions in the presence of concentrated sulfuric acid as a catalyst. The process for the production of trioxane known in the prior art is complex and comprises an extraction step which necessitates tedious solvent recovery steps. Furthermore, the process conventionally and commercially known in the prior art is time and energy consuming and leads to a low degree of conversion of the formaldehyde source into the desired cyclic acetals. Furthermore, the amount of side products formed by the process is high.

In view of the above, a need currently exists for an efficient process for producing cyclic acetals, such as trioxane. A need also exists for a process for producing cyclic acetals that has a relatively high conversion rate. A need also exists for a process for producing cyclic acetals from different formaldehyde sources.

SUMMARY

In general, the present disclosure is directed to a process for producing one or more cyclic acetals from a formaldehyde source. The process of the present disclosure is particularly well suited to producing a cyclic acetal, such as trioxane, from an aqueous formaldehyde solution. In other embodiments, however, the formaldehyde source may comprise gaseous formaldehyde, paraformaldehyde, polyoxymethylene homo- and copolymers, mixtures containing formaldehyde such as formaldehyde and trioxane mixtures, and blends thereof. The formaldehyde source is combined with an aprotic compound and contacted with a catalyst. The catalyst can be a heterogeneous catalyst. For instance, the catalyst may comprise a solid catalyst, such as an ion exchange material.

The reaction mixture may be contacted with a heterogeneous catalyst in a reactor under conditions that cause a portion of the formaldehyde to convert into a cyclic acetal to form a product stream, the product stream containing water, the cyclic acetal, unreacted formaldehyde, and the aprotic solvent. The product stream may be fed to a low pressure separating device. The low pressure separating device produces a cyclic acetal-rich gas stream and an aprotic solvent-rich liquid stream. Afterward, the cyclic acetal-rich gas stream may be quenched and subsequently fed to a distillation column for further separating the cyclic acetal from unreacted formaldehyde. The distillation column produces a cyclic acetal product stream containing the cyclic acetal in an amount of at least about 50% by weight and produces a formaldehyde-rich stream. The formaldehyde-rich stream and the aprotic solvent-rich stream may be recycled back to the reactor.

The amount of formaldehyde in the aqueous formaldehyde solution may vary. For example, the aqueous formaldehyde solution fed to the reactor may contain formaldehyde in an amount greater than about 65% by weight, such as in an amount greater than about 70% by weight, such as in an amount greater than about 75% by weight, such as in an amount greater than about 80% by weight.

Optionally, during the previously described process the aqueous formaldehyde solution may be fed through one or more concentrating devices.

In one embodiment, the reaction takes place in a fixed bed reactor. The reactor may operate at a temperature of from about 30° C. to about 200° C., such as from about 80° C. to about 120° C. and operating at a pressure of from about 0.15 bar to about 5 bar, such as from about 1 bar to about 2 bar.

The previously described process may be continuous or operated batch-wise.

In one embodiment, the heterogeneous catalyst may comprise an acid fixed on a solid support, the acid being a Lewis or a Broensted acid.

The low pressure separating device may operate adiabatically, operating at a pressure of greater than about 50 mbar, such as greater than about 150 mbar, such as greater than about 350 mbar, and generally less than about 600 mbar, such as less than about 500 mbar, such as less than about 400 mbar.

The aprotic compound may be polar. For instance, in one embodiment, the aprotic compound may be dipolar. In one embodiment, the aprotic compound comprises a sulfur containing organic compound such as a sulfoxide, a sulfone, a sulfonate ester, or mixtures thereof. In one embodiment, the aprotic compound comprises sulfolane. For example, the aprotic compound may comprise dimethyl sulfone. In another example, the aprotic compound comprises dimethyl sulfoxide.

The aprotic compound may also have a relatively high static permittivity or dielectric constant of greater than about 15. The aprotic compound may also be nitro-group free. In particular, compounds having nitro-groups may form undesired side reactions within the process.

The aprotic compound, for instance, may have a boiling point of greater than about 120° C., such as greater than about 140° C., such as greater than about 160° C., such as even greater than about 180° C. at a pressure of one bar. Preferably, the aprotic compound does not form an azeotrope with the cyclic acetal.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures in which.

Repeat use of reference characters in the present specification and drawings is intended to represent same or analogous features or elements of the present disclosure.

DETAILED DESCRIPTION

It is to be understood by one of ordinary skill in the art that the present discussion is a description of exemplary embodiments only, and is not intended as limiting the broader aspects of the present disclosure.

The present disclosure is generally directed to a process for producing a cyclic acetal. Of particular advantage, cyclic acetals can be produced from all different types of formaldehyde sources. As used herein, a formaldehyde source includes formaldehyde and oligomers or polymers formed from formaldehyde. Thus, a formaldehyde source can include paraformaldehyde, oxymethylene homopolymers, and oxymethylene copolymers. The process of the present disclosure is particularly well suited to forming a cyclic acetal from an aqueous formaldehyde solution. The aqueous formaldehyde solution can be formed from one of the formaldehyde sources described above.

The formaldehyde source is contacted with a catalyst in the presence of an aprotic compound to form a cyclic acetal. The aprotic compound facilitates production of the cyclic acetal in a manner that greatly enhances the conversion rates. Of particular advantage, the cyclic acetal produced according to the process can then be easily separated from the aprotic compound. For instance, in one embodiment, the cyclic acetal can be separated or isolated from the aprotic compound through a simple distillation process, since the aprotic compound may have a much higher boiling point than the cyclic acetal.

The catalyst that is used during conversion of the formaldehyde into the cyclic acetal can comprise a heterogeneous catalyst. The catalyst, for instance, can be immiscible in the aprotic compound and the formaldehyde source. In one embodiment, the catalyst comprises a solid catalyst. As used herein, a solid catalyst is a catalyst that includes at least one solid component. For instance, a catalyst may comprise an acid that is adsorbed or otherwise fixed to a solid support. The catalyst may also be present in liquid phase which is not miscible or is at least partially immiscible with the aprotic compound.

Various advantages and benefits are obtained when using a heterogeneous catalyst. For example, when using a heterogeneous catalyst, the catalyst can be easily separated from the aprotic compound, the formaldehyde source, and/or the cyclic acetal that is produced. In addition, in one embodiment a solid catalyst is used that remains in the reactor that is used to produce the cyclic acetal. In this manner, the catalyst can be used over and over again during the process.

Furthermore solid catalysts tend to be less corrosive to their environments e.g vessel walls.

Through the process of the present disclosure, a formaldehyde source may be converted into one or more cyclic acetals at extremely fast reaction times, such as within minutes. In addition, very high conversion rates can be achieved. For instance, in one embodiment, a majority of the formaldehyde source may be converted into one or more cyclic acetals.

In one embodiment, the aprotic compound is a liquid when contacted with the formaldehyde source. The formaldehyde source, on the other hand, may comprise a liquid formaldehyde solution. The formaldehyde source may dissolve into the aprotic compound or may be absorbed by the aprotic compound to form a homogeneous phase. The aprotic compound and the catalyst, in one embodiment, may comprise a liquid reaction mixture or a liquid medium.

The formaldehyde source reacts (converts) in the presence of the catalyst.

Cyclic acetals within the meaning of the present disclosure relate to cyclic acetals derived from formaldehyde. Typical representatives are represented the following formula:

wherein a is an integer ranging from 1 to 3.

Preferably, the cyclic acetals produced by the process of the present disclosure are trioxane (a=1) and/or tetroxane (a=2). Trioxane and tetroxane usually form the major part (at least 80 wt.-%, preferably at least 90 wt.-%) of the cyclic acetals formed by the process of the present disclosure.

The weight ratio of trioxane to tetroxane varies with the heterogeneous catalyst used. Typically, the weight ratio of trioxane to tetroxane ranges from about 3:1 to about 40:1, preferably about 4:1 to about 20:1.

The process of the invention is carried out in the presence of a heterogeneous catalyst for the conversion of the formaldehyde source into cyclic acetals. Suitable catalysts are any components which accelerate the conversion of the formaldehyde source to the cyclic acetals. The catalyst is a catalyst for the conversion (reaction) of a formaldehyde source into cyclic acetals, preferably into trioxane and/or tetroxane.

Usually, cationic catalysts can be used for the process of the invention. The catalysts can be a solid catalyst or an immiscible liquid catalyst. A typical liquid immiscible catalyst is a liquid acidic ion exchange resin. Solid catalyst means that the catalyst is at least partly, preferably completely in solid form under the reaction conditions. Typical solid catalysts which may be used for the process of the present invention are acid ion-exchange material, strongly acidic ion-exchange material, Lewis acids and/or Broensted acids fixed on a solid support, wherein the support may be an inorganic material such as $SiO_2$ or organic material such as organic polymers.

Preferred catalysts that may be fixed to a solid support are selected from the group consisting of Broensted acids and Lewis acids. The catalyst can be selected from the group consisting of trifluoroalkanesulfonic acids such as trifluoromethanesulfonic acid, perchloric acid, methanesulfonic acid, toluenesulfonic acid and sulfuric acid, or derivatives thereof such as anhydrides or esters or any other derivatives that generate the corresponding acid under the reaction conditions. Lewis acids like boron trifluoride, arsenic pentafluoride can also be used. Heteropolyacides such as tungsten heteropoly acides (e.g. tungstophosphates) may also be used. It is also possible to use mixtures of all the individual catalysts mentioned above.

In one embodiment, the heterogeneous catalyst may comprise a Lewis or Broensted acid species dissolved in an inorganic molten salt. The molten salt may have a melting point below 200° C., such as less than about 100° C., such as less than about 30° C. The molten salt can then be immobilized or fixed onto a solid support as described above. The solid support, for instance, may be a polymer or a solid oxide. An example of an organic molten salt includes ionic liquids. For instance, the ionic liquid may comprise 1-n-alkyl-3-methylimidazolium triflate. Another example is 1-n-alkyl-3-methylimidazolium chloride.

In one embodiment, the acidic compound present in the catalyst can have a pKa below 0, such as below about −1, such as below about −2, when measured in water at a temperature of 18° C. The pKa number expresses the strength of an acid and is related to the dissociation constant for the acid in an aqueous solution.

Examples of heterogeneous catalysts that may be used according to the present disclosure include the following:

(1) solid catalysts represented by acidic metal oxide combinations which can be supported onto usual carrier materials such as silica, carbon, silica-alumina combinations or alumina. These metal oxide combinations can be used as such or with inorganic or organic acid doping. Suitable examples of this class of catalysts are amorphous silica-alumina, acid clays, such as smectites, inorganic or organic acid treated clays, pillared clays, zeolites, usually in their protonic form, and metal oxides such as $ZrO_2$—$TiO_2$ in about 1:1 molar combination and sulfated metal oxides e.g. sulfated $ZrO_2$. Other suitable examples of metal oxide combinations, expressed in molar ratios, are: $TiO_2$—$SiO_2$ 1:1 ratio; and $ZrO_2$—$SiO_2$ 1:1 ratio.

(2) several types of cation exchange resins can be used as acid catalyst to carry out the reaction. Most commonly, such resins comprise copolymers of styrene, ethylvinyl benzene and divinyl benzene functionalized so as to graft $SO_3H$ groups onto the aromatic groups. These acidic resins can be used in different physical configurations such as in gel form, in a macro-reticulated configuration or supported onto a carrier material such as silica or carbon or carbon nanotubes. Other types of resins include perfluorinated resins carrying carboxylic or sulfonic acid groups or both carboxylic and sulfonic acid groups. Known examples of such resins are: NAFION™, and AMBERLYST resins. The fluorinated resins can be used as such or supported onto an inert material like silica or carbon or carbon nanotubes entrapped in a highly dispersed network of metal oxides and/or silica.

(3) heterogeneous solids, having usually a lone pair of electrons, like silica, silica-alumina combinations, alumina, zeolites, silica, activated charcoal, sand and/or silica gel can be used as support for a Broensted acid catalyst, like methane sulfonic acid or para-toluene sulfonic acid, or for a compound having a Lewis acid site, such as $SbF_5$, to thus interact and yield strong Broensted acidity. Heterogeneous solids, like zeolites, silica, or mesoporous silica or polymers like e.g. polysiloxanes can be functionalized by chemical grafting with a Broensted acid group or a precursor therefore to thus yield acidic groups like sulfonic and/or carboxylic acids or precursors therefore. The functionalization can be introduced in various ways known in the art like: direct grafting on the solid by e.g. reaction of the SiOH groups of the silica with chlorosulfonic acid; or can be attached to the solid by means of organic spacers which can be e.g. a perfluoro alkyl silane derivative. Broensted acid functionalized silica can also be prepared via a sol gel process, leading to e.g. a thiol functionalized silica, by co-condensation of $Si(OR)_4$ and e.g. 3-mercaptopropyl-tri-methoxy silane using either neutral or ionic templating methods with subsequent oxidation of the thiol to the corresponding sulfonic acid by e.g. $H_2O_2$. The functionalized solids can be used as is, i.e. in powder form, in the form of a zeolitic membrane, or in many other ways like in admixture with other polymers in membranes or in the form of solid extrudates or in a coating of e.g. a structural inorganic support e.g. monoliths of cordierite; and (4) heterogeneous heteropolyacids having most commonly the formula $H_xPM_yO_z$. In this formula, P stands for a central atom, typically silicon or phosphorus. Peripheral atoms surround the central atom generally in a symmetrical manner. The most common peripheral elements, M, are usually Mo or W although V, Nb, and Ta are also suitable for that purpose. The indices xyz quantify, in a known manner, the atomic proportions in the molecule and can be determined routinely. These polyacids are found, as is well known, in many crystal forms but the most common crystal form for the heterogeneous species is called the Keggin structure. Such heteropolyacids exhibit high thermal stability and are non-corrosive. The heterogeneous heteropolyacids are preferably used on supports selected from silica gel, kieselguhr, carbon, carbon nanotubes and ion-exchange resins. A preferred heterogeneous heteropolyacid herein can be represented by the formula $H_3PM_{12}O_{40}$ wherein M stands for W and/or Mo. Examples of preferred PM moieties can be represented by $PW_{12}$, $PMo_{12}$, $PW_{12}/SiO_2$, $PW_{12}/carbon$ and $SiW_{12}$.

As described above, formaldehyde or a formaldehyde source is converted to a cyclic acetal by contacting the formaldehyde source with aprotic compound and a catalyst. A gas or liquid stream may be fed to the reactor that contains formaldehyde in combination with other components. For instance, the formaldehyde may be present with trioxane, or other monomers used to produce polyoxymethylene polymers. In yet another embodiment, the formaldehyde source may comprise an aqueous formaldehyde solution. The aqueous formaldehyde solution, for instance, may contain water in amounts greater than about 10%, such as in amounts greater than about 15%, such as in amounts from about 10% to about 50%.

As used herein, an aprotic compound is a compound that does not contain any substantial amounts of hydrogen atoms which can disassociate. In one embodiment, the aprotic compound is liquid under the reaction conditions. Therefore, the aprotic compound may have a melting point of about 180° C. or less, preferably about 150° C. or less, more preferably about 120° C. or less, especially about 60° C. or less.

For practical reasons, it is advantageous to use an aprotic compound which has a melting point in the order of preference (the lower the melting point the more preferred) of below about 50° C., below about 40° C. and below about 30° C. and below about 20° C. Especially, aprotic compounds which are liquid at about 25 or about 30° C. are suitable since they can be easily transported by pumps within the production plant.

Further, the aprotic compound may have a boiling point of about 120° C. or higher, preferably about 140° C. or higher, more preferably about 160° C. or higher, especially about 180° C. or higher, determined at 1 bar. In a further embodiment the boiling point of the aprotic compound is about 200° C. or higher, preferably about 230° C. or higher, more preferably about 240° C. or higher, further preferably about 250° C. or higher and especially about 260° C. or higher or 270° C. or higher. The higher the boiling point the better the cyclic acetals, especially trioxane and/or tetroxane, formed by the process of the present disclosure can be separated by distillation. Therefore, according to an especially preferred embodiment of the present disclosure the boiling point of the aprotic compound is at least about 20° C. higher than the boiling point of the cyclic acetal formed, in particular at least about 20° C. higher than the boiling point of trioxane and/or tetroxane.

Additionally, aprotic compounds are preferred which do not form an azeotrope with the cyclic acetal, especially do not form an azeotrope with trioxane.

In a preferred embodiment of the present invention the reaction mixture or liquid medium in the reactor comprises at least about 20 wt.-%, preferably at least about 40 wt.-%, more preferably at least about 60 wt.-%, most preferably at least about 80 wt.-% and especially at least about 90 wt.-% of the aprotic compound(s), wherein the weight is based on the total weight of the reaction mixture. The liquid medium or the reaction mixture or the liquid mixture (A) may comprise one or more aprotic compound(s).

In a preferred embodiment the liquid medium is essentially consisting of the aprotic compound. Essentially consisting of means that the liquid medium comprises at least about 95 wt.-%, preferably at least about 98 wt.-%, more preferably at least about 99 wt.-%, especially at least about 99.5 wt.-%, in particular at least about 99.9 wt.-% of the aprotic compound(s). In a further embodiment of the invention the liquid medium is the aprotic compound, i.e., the liquid medium is consisting of the aprotic compound.

It has been found that liquid aprotic compounds which at least partly dissolve or absorb the formaldehyde source lead to excellent results in terms of conversion of the formaldehyde source into the desired cyclic acetals.

Therefore, aprotic compounds are preferred which at least partly dissolve or absorb the formaldehyde source under the reaction conditions. Preferred are aprotic compounds which dissolve paraformaldehyde (98 wt.-% formaldehyde, 2 wt.-% water) [can also be expressed as Pn=moles of formaldehyde/moles of water=(98/30)/(2/18)=approx. 29] at the reaction temperature in an amount of at least about 0.1 wt.-%, wherein the weight is based on the total weight of the solution.

The aprotic compound used in the process can be a polar aprotic compound, especially a dipolar compound. Polar aprotic solvents are much more suitable to dissolve the formaldehyde source. Non-polar aprotic compounds such as unsubstituted hydrocarbons (e.g. cyclic hydrocarbons such as cyclohexane, or alicyclic hydrocarbons such as hexane, octane, decane, etc.) or unsubstituted unsaturated hydrocarbons or unsubstituted aromatic compounds are less suitable. Therefore, according to a preferred embodiment the aprotic compound is not an unsubstituted hydrocarbon or unsubstituted unsaturated hydrocarbon or unsubstituted aromatic compound. Further, preferably the reaction mixture comprises unsubstituted hydrocarbons and/or unsubstituted unsaturated hydrocarbons and/or unsubstituted aromatic compounds in an amount of less than about 50 wt.-%, more preferably less than about 25 wt.-%, further preferably less than about 10 wt.-%, especially less than about 5 wt.-%, e.g. less than about 1 wt.-% or about 0 wt.-%.

Halogen containing compounds are less preferred due to environmental aspects and due to their limited capability to dissolve the formaldehyde sources. Further, the halogenated aliphatic compounds may cause corrosions in vessels or pipes of the plant and it is difficult to separate the cyclic acetals formed from the halogenated compounds.

According to one embodiment, the aprotic compound is halogen free. In a further preferred embodiment the reaction mixture comprises less than about 50 wt.-%, more preferably less than about 25 wt.-%, further preferably less than 10 wt.-%, more preferably less than 5 wt.-%, especially less than 1 wt.-% or less than 50 ppm of halogenated compounds.

Likewise, the use of (liquid) sulphur dioxide not only requires unacceptable energy usage but also leads to difficulties with isolation of the cyclic acetals. Therefore, the aprotic compound is preferably free of sulphur dioxide. In a further preferred embodiment the reaction mixture comprises less than about 50 wt.-%, more preferably less than about 25 wt.-%, further preferably less than 10 wt.-%, more preferably less than 5 wt.-%, especially less than 1 wt.-% or 0 wt.-% of sulphur dioxide.

Polar aprotic compounds are especially preferred. According to a preferred embodiment of the invention the aprotic compound has a relative static permittivity of more than about 15, preferably more than about 16 or more than about 17, further preferably more than about 20, more preferably of more than about 25, especially of more than about 30, determined at 25° C. or in case the aprotic compound has a melting point higher than 25° C. the relative permittivity is determined at the melting point of the aprotic compound.

The relative static permittivity, $\varepsilon_r$, can be measured for static electric fields as follows: first the capacitance of a test capacitor $C_0$, is measured with vacuum between its plates. Then, using the same capacitor and distance between its plates the capacitance $C_x$ with an aprotic compound between the plates is measured. The relative dielectric constant can be then calculated as $$\varepsilon_r = \frac{C_x}{C_0}.$$

Within the meaning of the present invention the relative permittivity is determined at 25° C. or in case the aprotic compound has a melting point higher than 25° C. the relative permittivity is determined at the melting point of the aprotic compound.

According to a further aspect of the invention the aprotic compound is a dipolar aprotic compound.

The aprotic compound within the meaning of the present invention is generally a dipolar and non-protogenic compound which has a relative permittivity as defined above of more than 15, preferably more than 25 or more than 30, determined at 25° C. or in case the aprotic compound has a melting point higher than 25° C. the relative permittivity is determined at the melting point of the aprotic compound.

The process can be carried out in manner wherein the formaldehyde source is completely dissolved or absorbed in the liquid medium or reaction mixture or liquid mixture (A).

Therefore, according to one embodiment the formaldehyde source and the aprotic compound form a homogenous phase under the reaction conditions. Suitable aprotic compounds are selected from the group consisting of organic sulfoxides, organic sulfones, organic sulfonate ester, and mixtures thereof.

According to a preferred embodiment the aprotic compound is selected from sulfur containing organic compounds. The sulfur containing organic compound may comprise, for instance, sulfolane, dimethyl sulfone, dimethyl sulfoxide, or mixtures thereof.

The aprotic compound is preferably selected from the group consisting of cyclic or alicyclic organic sulfoxides, alicyclic or cyclic sulfones, and mixtures thereof. Excellent results can be achieved by aprotic compounds as represented by the following formula (I):

(I)

wherein
n is an integer ranging from 1 to 6, preferably 2 or 3, and wherein the ring carbon atoms may optionally be substituted by one or more substituents, preferably selected from $C_1$-$C_8$-alkyl which may be branched or unbranched. Preferred compounds of formula (I) are sulfolane, methylsulfolane, dimethylsulfolane, ethylsulfolane, diethylsulfolane, propylsulfolane, dipropylsulfolane, butylsulfolane, dibutylsulfolane, pentylsulfolane, dipentylsulfolane, and hexylsulfolane as well as octylsulfolane.

According to the most preferred embodiment the aprotic compound is sulfolane (tetrahydrothiophene-1,1-dioxide).

Sulfolane is an excellent solvent for the formaldehyde source, it is stable under acidic conditions, it does not deactivate the catalysts and it does not form an azeotrope with trioxane. Further, it is a solvent which is inert under the reaction conditions.

Unless indicated otherwise the expression "reaction mixture" refers to the mixture which is used for the reaction of the formaldehyde source to the cyclic acetals. The concentrations and amounts of the individual components of the reaction mixture refer to the concentrations and amounts at the beginning of the reaction. In other words the reaction mixture is defined by the amounts of its starting materials, i.e. the amounts of initial components.

Likewise the amounts defined for the "liquid mixture" refer to the amounts of the components at the beginning of the reaction, i.e. prior to the reaction.

The formaldehyde source reacts to the cyclic acetals and, as a consequence, the concentration of the formaldehyde source decreases while the concentration of the cyclic acetals increases.

At the beginning of the reaction a typical reaction mixture of the invention comprises a formaldehyde source which is at least partly, preferably completely dissolved or absorbed in sulfolane.

Further, an especially preferred embodiment of the present invention is a process for producing cyclic acetal comprising reacting a formaldehyde source in the presence of a catalyst wherein the reaction is carried out in sulfolane or a process for producing cyclic acetals from a formaldehyde source in the presence of a catalyst and sulfolane.

A further preferred aprotic compound is represented by formula (II):

(II)

wherein $R^1$ and $R^2$ are independently selected from $C_1$-$C_8$-alkyl which may be branched or unbranched, preferably wherein $R^1$ and $R^2$ independently represent methyl or ethyl. Especially preferred is dimethyl sulfone.

According to a further preferred embodiment the aprotic compound is represented by formula (III):

(III)

wherein
n is an integer ranging from 1 to 6, preferably 2 or 3, and wherein the ring carbon atoms may optionally be substituted by one or more substituents, preferably selected from $C_1$-$C_8$-alkyl which may be branched or unbranched.

Suitable aprotic compounds are also represented by formula (IV):

(IV)

wherein $R^3$ and $R^4$ are independently selected from $C_1$-$C_8$-alkyl which may be branched or unbranched, preferably wherein $R^1$ and $R^2$ independently represent methyl or ethyl.

Especially preferred is dimethyl sulfoxide.

Suitable aprotic compounds may be selected from aliphatic dinitriles, preferably adiponitrile.

In a further aspect of the invention a mixture of two or more aprotic compounds is used. A mixture of aprotic compounds may be used to decrease the melting point of the aprotic medium. In a preferred embodiment the aprotic compound comprises or is consisting of a mixture of sulfolane and dimethyl sulfoxide.

Advantageously, the aprotic compound does not essentially deactivate the catalyst. Preferably, under the reaction conditions the aprotic compound does essentially not deactivate the catalyst used in the process of the present invention. Aprotic solvents such as dimethylformamide (DMF), dimethylacetamide (DMAC) or N-methylpyrrolidone (NMP) are too basic and therefore may deactivate the catalyst and, as a consequence, said solvents are less suitable. According to a preferred embodiment of the present invention the liquid reaction mixture is essentially free of amides, preferably essentially free of acrylic or cyclic amides. Essentially free means that the amides may be present in an amount of less than about 5 wt.-%, preferably less than about 2 wt.-%, more preferably less than 0.5 wt.-%, especially less than about 0.01 wt.-% and, in particular, less than 0.001 wt.-% or about 0 wt.-%, wherein the weight is based on the total weight of the liquid reaction mixture.

Nitro group containing compounds can lead to undesired side products or even demonstrate an insufficient solubility for the formaldehyde sources.

Therefore, the aprotic compound preferably does not comprise a nitro group and/or a nitrogen atom. Further, according to a preferred embodiment of the present invention the aprotic compound is a non-aromatic aprotic compound. Especially, the aprotic compound is not nitrobenzene or an aromatic nitro compound. Further, preferably, the aprotic compound does not comprise ether.

Within the meaning of the present invention the aprotic compound does not deactivate the catalyst if under the reaction conditions less than about 95%, preferably less than about 50%, more preferably less than about 10%, of the Broensted acid catalyst used protonates the aprotic compound. In case a Lewis acid catalyst is used the aprotic compound does not deactivate the catalyst if under the reaction conditions less than about 90 wt-%, preferably less than about 50 wt.-%, more preferably less than about 10 wt-% of the Lewis acid catalyst forms a complex with the aprotic compound.

The degree of protonation and complex formation can be determined by NMR spectroscopy such as $^1$H or $^{13}$C-NMR. The degree of protonation and complex formation is determined at 250° C., preferably in $d_6$-DMSO.

The deactivation of the catalyst can also be determined in the following manner:

10 g of commercially available paraformaldehyde (95 wt-%) is dissolved in 100 g of sulfolane at a temperature sufficient to dissolve the paraformaldehyde in such a way that no gaseous formaldehyde can escape. The clear solution is kept at 90° C. and 0.1 wt-% of triflic acid is added. The rate of the formation of trioxane is measured (by measuring the concentration of trioxane as a function of time).

The same experiment is repeated, except that 10 g of the sulfolane are replaced by 10 g of the aprotic compound to be tested. If the rate of trioxane formation is still greater than about 1%, preferably greater than about 5%, more preferably greater than about 10%, of the rate of the initial experiment then it is concluded that the aprotic compound in question does not deactivate the catalyst (even though it may reduce its activity).

The aprotic compound should not be too basic in order to avoid deactivation of the catalysts. On the other hand the aprotic compound preferably does not chemically react with the formaldehyde source under the reaction conditions, i.e. is an inert aprotic compound.

Preferably, under the reaction conditions the aprotic compound should not react chemically with the formaldehyde source or the cyclic acetal obtained by the process of the invention. Compounds like water and alcohols are not suitable as they react with formaldehyde. Within the meaning of the present invention an aprotic compound does not chemically react with the formaldehyde source when it meets the following test criteria:

5 g of commercially available paraformaldehyde (95 wt.-%) is added to 100 g of the aprotic compound containing 0.1 wt.-% trifluoromethanesulfonic acid and heated at 120° C. for 1 hour with stirring in a closed vessel so that no gaseous formaldehyde can escape. If less than about 1 wt.-%, preferably less than about 0.5 wt.-%, more preferably less than about 0.1 wt.-% and most preferably less than about 0.01 wt.-% of the aprotic compound has chemically reacted, then the aprotic compound is considered not to have reacted with the formaldehyde source. If the aprotic compound meets the criteria it is considered inert.

Further, under the acidic reaction conditions the aprotic compound should be essentially stable. Therefore, aliphatic ethers or acetals are less suitable as aprotic compounds. The aprotic compound is considered stable under acidic conditions within the meaning of the present invention if the aprotic compound meets the following test conditions:

100 g of the aprotic compound to be tested containing 0.5% by weight (wt.-%) trifluoromethanesulfonic acid is heated at 120° C. for 1 hour. If less than about 0.5 wt.-%, preferably less than about 0.05 wt.-%, more preferably less than about 0.01 wt.-% and most preferably less than about 0.001 wt.-% of the aprotic compound has chemically reacted, then the aprotic compound is considered to be stable under acidic conditions.

The process of the invention can also be used to change the ratio of cyclic acetals derived from formaldehyde. Therefore, the formaldehyde source can also comprise cyclic acetals selected from the group consisting of trioxane, tetroxane and cyclic oligomers derived from formaldehyde.

Preferably, the reaction mixture comprises the formaldehyde source in an amount ranging from about 0.1 to about 60 wt-% or about 1 to less than about 30 wt.-%, more preferably from about 5 to about 15 wt-%, further preferably ranging from about 7 to about 13 wt-% and most preferred ranging from about 8 to about 12 wt-%, especially ranging from 30 to 60 wt.-% based on the total weight of the reaction mixture.

It has been found that especially good results in terms of conversion can be achieved when the weight ratio of formaldehyde/water of the formaldehyde source is greater than 4, preferable greater than 5, and most preferably greater than 5.5.

Typically, the reaction is carried out at a temperature higher than about 0° C., preferably ranging from about 30° C. to about 170° C., more preferably ranging from about 40° C. to about 140° C., further preferably from about 40° C. to about 120° C. and most preferably from about 50° C. to about 110° C.

The pressure during the reaction can generally be from about 10 millibars to about 20 bars, such as from about 0.5 bar to about 10 bar, such as from about 0.5 bar to about 2 bar.

A further advantage of the process of the present invention is that the cyclic acetals can easily be separated from the reaction mixture. The cyclic acetal, especially the trioxane can be separated from the reaction mixture by distillation in a high purity grade. Especially in case aprotic compounds (such as sulfolane) having a boiling point higher than about 20° C. above the boiling point of the cyclic acetals is used the formed cyclic acetals can simply be distilled off. In case sulfolane is used as the aprotic compound the formed trioxane can be distilled off without the formation of an azeotrope of sulfolane with trioxane.

The separation of the cyclic acetals enables the unreacted compounds in the reaction mixture to be recycled into the reaction process.

For example, in accordance with the present disclosure, the reaction mixture may be contacted with a heterogeneous catalyst in a reactor under conditions that cause a portion of the formaldehyde to convert into a cyclic acetal to form a product stream, the product stream containing water, the cyclic acetal, unreacted formaldehyde, and the aprotic solvent.

The product stream may then be fed to a low pressure separating device, such as a flash drum. The low pressure separating device produces a cyclic acetal-rich gas stream and an aprotic solvent-rich liquid stream. Afterward, the cyclic acetal-rich gas stream may be quenched and subsequently fed to a distillation column for further separating the cyclic acetal from unreacted formaldehyde. The distillation column produces a cyclic acetal product stream containing the cyclic acetal in an amount of at least about 65% by weight. The distillation column also produces a formaldehyde-rich stream. The formaldehyde-rich stream and the aprotic solvent-rich stream may be recycled back to the reactor.

The process of the invention can be carried out batch wise or as a continuous process.

In a preferred embodiment the process is carried out as a continuous process wherein the formaldehyde source is continuously fed to the liquid medium comprising the catalyst and wherein the cyclic acetals, e.g. the trioxane, is continuously separated (isolated) by separation methods such as distillation.

The process of the invention leads to an extremely high conversion of the formaldehyde source to the desired cyclic acetals.

According to a preferred embodiment the final conversion of the formaldehyde source to the cyclic acetal is greater than 10%, based on initial formaldehyde source.

The final conversion refers to the conversion of the formaldehyde source into the cyclic acetals in the liquid system. The final conversion corresponds to the maximum conversion achieved in the liquid system.

The final conversion of the formaldehyde source to the cyclic acetals can be calculated by dividing the amount of cyclic acetals (expressed in wt.-%, based on the total weight of the reaction mixture) in the reaction mixture at the end of the reaction divided by the amount of formaldehyde source (expressed in wt.-%, based on the total weight of the reaction mixture) at the beginning of the reaction at t=0.

For example the final conversion of the formaldehyde source to trioxane can be calculated as:

Final conversion=(amount of trioxane in the reaction mixture expressed in weight-% at the end of the reaction)/(amount of formaldehyde source in the reaction mixture expressed in weight-% at $t=0$ [initial amount of formaldehyde source in the reaction mixture]).

According to a further preferred embodiment of the process of the invention the final conversion of the formaldehyde source into the cyclic acetals, preferably trioxane and/or tetroxane, is higher than 12%, preferably higher than 14%, more preferably higher than 16%, further preferably higher than 20%, especially higher than 30%, particularly higher than 50%, for example higher than 80% or higher than 90%.

Figure 1:
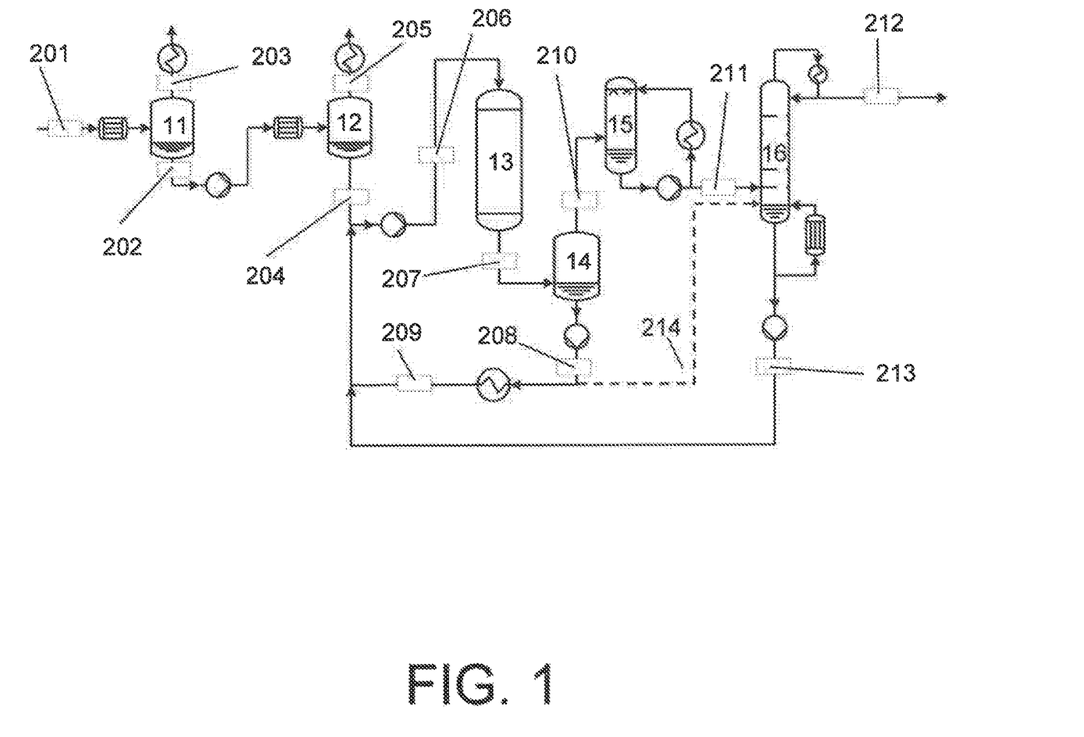
FIG. 1 is a schematic diagram of one embodiment of a process in accordance with the present disclosure.

The process for producing cyclic acetals in accordance with the present disclosure can be conducted continuously or can be conducted in a batch-wise manner (discontinuous). Referring to FIG. 1, one embodiment of a continuous process for producing a cyclic acetal in accordance with the present disclosure is shown. The process illustrated in FIG. 1 is particularly well suited for converting anhydrous formaldehyde gas into a cyclic acetal such as trioxane. It should be understood, however, that the process in FIG. 1 may also be used to process any of the formaldehyde sources described above.

In FIG. 1, an aqueous formaldehyde inlet stream 201 is fed into an optional first formaldehyde concentrator 11, which has two outputs: a first concentrated formaldehyde stream 202 and a first dilute formaldehyde stream 203. The first concentrated formaldehyde stream 202 is passed into an optional second formaldehyde concentrator 12, which also has two outputs: a second concentrated formaldehyde stream 204 and a second dilute formaldehyde stream 205. The first and second formaldehyde concentrators may include auxiliary heating and condensers. The dilute streams may be reprocessed to return residual formaldehyde into the aqueous formaldehyde inlet stream 201.

The second concentrated formaldehyde stream 204 is combined with the formaldehyde-rich recycle stream 213 and the heated aprotic solvent-rich recycle stream 209 to form a reactor inlet stream 206 which is fed into the reactor 13.

The reactor outlet stream 207 is passed into a low pressure separating device 14, which has two outputs: the aprotic solvent-rich recycle stream 208 and the cyclic acetal-rich gas stream 210.

The cyclic acetal-rich gas stream 210 is fed into a quench column 15. The quench column may include auxiliary heating and condensers. The quench column feeds the quenched cyclic acetal-rich stream 211 to a reactor column 16. The reactor column 16 may distill the quenched cyclic acetal-rich stream 211 and provide a product stream 212 and a formaldehyde-rich recycle stream 213.

Optionally, a small fraction of the aprotic solvent-rich recycle stream 208 may be diverted into a stabilizing aprotic solvent-rich stream 214 to stabilize the concentrated formaldehyde solution processed by the reactor column 16.

In one embodiment, for instance, a liquid aprotic compound is fed to the reactor 13 that is not heated and is at a temperature of less than about 50° C., such as less than about 40° C., such as less than about 25° C. Generally, the liquid aprotic compound fed to the reactor is at a temperature greater than about 0° C., such as greater than about 5° C., such as greater than about 10° C., such as greater than about 15° C.

The fixed bed reactor 13, in one embodiment, can contain a solid catalyst. The catalyst bed can be placed above, below, or in between inert materials, such as solid oxides, or a mixture of solid oxides. The inert materials may improve the radial distribution of the gas/liquid stream and avoid loss of catalyst. Use of the inert material, however, is optional.

In one embodiment, the fixed bed reactor 13 is operated as a continuous-liquid trickle bed reactor. For instance, the gas and the liquid velocity can be selected such that a trickle flow regime or a pulsating regime is achieved. Superficial liquid velocities can be between about 5 m/hr to about 20 m/hr, such as from about 15 m/hr to about 100 m/hr. The liquid-gas mass ratio at the reactor inlet can be between about 2 kg/kg to about 30 kg/kg, such as from about 5 kg/kg to about 10 kg/kg.

The temperature of the reactor inlet stream 206 may be from about about 30° C. to about 200° C., such as from about 80 C to about 120° C. The temperature within the reactor 13 can be from about 30° C. to about 200° C., such as from about 80 C to about 120° C.

The pressure within the reactor 13 can generally be from about 0.15 bar to about 5 bar (absolute), such as from about 1 bar to about 2 bar.

Within the fixed bed reactor 13, the formaldehyde source is converted into a cyclic acetal.

In an alternative embodiment, the process includes a stirred tank reactor 13 that contains a suspended solid catalyst material. The catalyst concentration within the reactor can be less than about 75% by weight, such as less than about 50% by weight, such as less than about 30% by weight, such as less than about 3% by weight. Generally, however, the suspended catalyst concentration within the reactor is greater than 0% by weight, such as greater than about 0.5% by weight, such as greater than about 1% by weight. The suspended catalyst is retained by means of filtration inside the reactor or by means of cross flow filtration outside the reactor. A formaldehyde source is fed to the reactor 13 through an input. The formaldehyde source, which may comprise formaldehyde gas, is dispersed within the reactor by means of stirring. The stirring power input to the system can be from about 0.01 kW/m$^3$, to about 20 kW/m$^3$, such as from about 0.1 kW/m$^3$, to about 3 kW/m$^3$.

The low pressure separating device 14 may return varying amounts of the aprotic solvent into the aprotic solvent-rich recycle stream 208. For example, the aprotic solvent-rich recycle stream 208 may contain the aprotic solvent in an amount of at least about 20% by weight, such as greater than about 30% by weight, such as greater than about 40% by weight, such as greater than about 50% by weight, such as greater than about 60% by weight. Generally, the aprotic solvent-rich recycle stream 208 may contain the aprotic solvent in an amount of less than about 95% by weight, such as less than about 90% by weight, such as less than about 80% by weight, such as less than about 70% by weight.

Preferably, in some embodiments, the low pressure separating device 14 separates as much trioxane being formed over the catalyst bed as possible while retaining the solvent and formaldehyde-water oligomers. The low pressure separating device 14 may be a flash separation vessel which is operated adiabatically at pressure above 50 mbar absolute, better above 150 mbar absolute and preferred at 350 mbar absolute. Generally, the operation pressure is below 3 bar absolute, such as less than about 2 bar absolute, such as less than about 1 bar absolute. The rapid flash operation in the absence of acid catalyst may enable the retention the high boiling point component which is mostly sulfolane and formaldehyde-water oligomers.

The formaldehyde-rich recycle stream 213 exiting the reactor column 16 may contain varying amounts of formaldehyde, preferably containing formaldehyde in an amount of at least about 50% by weight, such as about 55% by weight, such as about 60% by weight, such as about 65% by weight, such as about 70% by weight, such as about 80% by weight, such as about 95% by weight. Generally, the formaldehyde-rich recycle stream 213 contains formaldehyde in an amount less than about 99% by weight, such as less than about 95% by weight, such as less than about 90% by weight.

As a result of extracting the cyclic acetal with the low pressure separating device 14 and the reactor column 16, the process as shown in FIG. 1 may retain much of the aprotic solvent originally in the system, and, in some embodiments, only need infrequent resupply. For example, although the aprotic solvent may generally be found in the product stream 212 in some amount greater than 0% by weight, the aprotic solvent lost in the product stream 212 may be lower than about 20% by weight, or lower than about 10% by weight, or lower than about 5% by weight, such as about 4% by weight, such as about 2% by weight, such as about 1% by weight, or lower.

The product stream 212 preferably contains the cyclic acetal in an amount of at least about 50% by weight, such as about 55% by weight, such as about 60% by weight, such as about 65% by weight, such as about 70% by weight, such as about 80% by weight, such as about 95% by weight, such as about 99% by weight. Generally, however, the product stream 212 contains the cyclic acetal in an amount less than about 99.9% by weight, such as less than about 95% by weight, such as less than about 80% by weight.

Through the process shown in FIG. 1, for instance, formaldehyde conversion to the cyclic acetal can be greater than about 50%, such as greater than about 70%, such as greater than about 90%. In one embodiment, for instance, more than 95%, such as more than 98%, such as even more than 99% of the formaldehyde source may be converted into a cyclic acetal. Generally, however, less than 100% by weight of the formaldehyde source is converted into a cyclic acetal.

Figure 2:
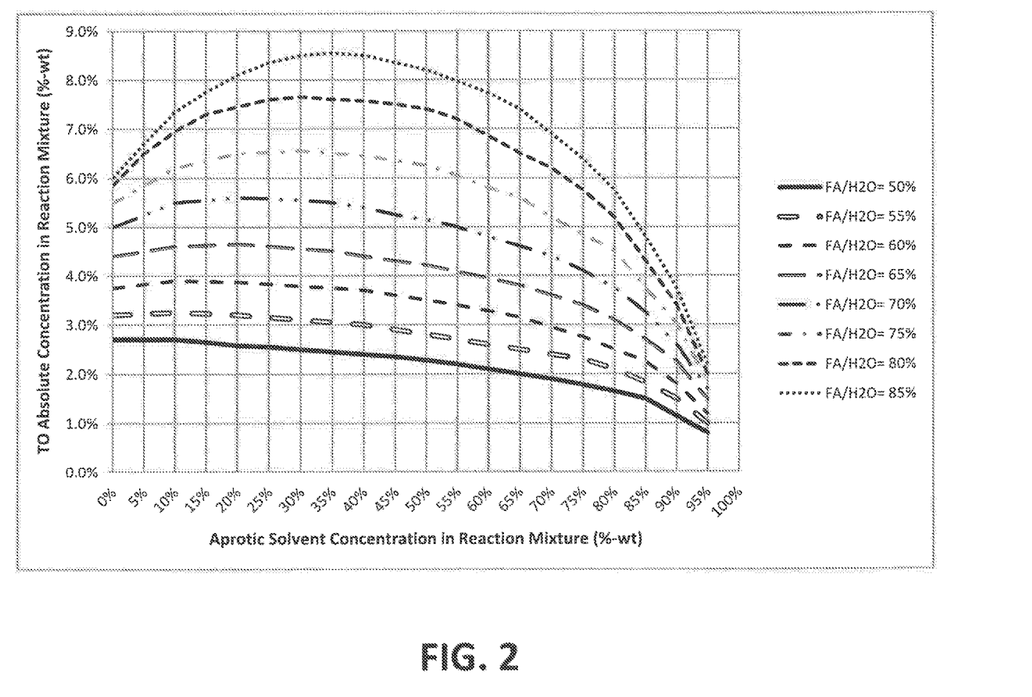
FIG. 2 is a chart tracking the results of an example process executed in accordance with the present disclosure.

FIG. 2 is a graphical representation of one example embodiment. In particular, FIG. 2 charts the trioxane absolute concentration in the reaction mixture, expressed in weight percent, as a function of the aprotic solvent absolute concentration in the reaction mixture, also expressed in weight percent, as measured in one embodiment. Curves and points are plotted for various concentrations of formaldehyde in the aqueous formaldehyde solution.

As shown, the trioxane concentration is raised by increasing the concentration of formaldehyde in the aqueous formaldehyde solution. For example, the highest trioxane concentration was observed when the aqueous formaldehyde solution contained 85% formaldehyde by weight, for a formaldehyde to water ratio of 5.7:1. Preferably, the formaldehyde is present in the aqueous formaldehyde solution in an amount greater than about 30% by weight, such as greater than about 60% by weight, such as about 70% by weight, such as about 80% by weight. More preferably, the formaldehyde is present in the aqueous formaldehyde solution in an amount greater than about 85% by weight, such as about 90% by weight, such as about 95% by weight. Generally, however, the formaldehyde is present in the aqueous solution in an amount less than 100% by weight of the solution.

Cyclic acetals made according to the present disclosure can be used in numerous and diverse applications. In one embodiment, for instance, the cyclic acetals produced by the present disclosure may be used to produce an oxymethylene polymer.

The oxymethylene polymer production process may comprise any suitable process for producing oxymethylene homopolymers and/or copolymers. The polymer production process, for instance, may comprise an anionic polymerization process or a cationic polymerization process. The process for producing the oxymethylene polymer may comprise a heterogeneous process where the polymer precipitates in a liquid, may comprise a homogeneous process such as a bulk polymerization process that forms a molten polymer or may be a polymer process that includes both a heterogeneous phase and a homogeneous phase.

For the preparation of oxymethylene polymers, a monomer that forms —$CH_2$—O— units or a mixture of different monomers, are reacted in the presence of an initiator. Examples of monomers that form —$CH_2$O-units are formaldehyde or its cyclic oligomers, such as 1,3,5-trioxane (trioxane) or 1,3,5,7-tetraoxocane.

The oxymethylene polymers are generally unbranched linear polymers which generally contain at least 80 mol %, preferably at least 90 mol %, in particular at least 95 mol %, of oxymethylene units (—$CH_2$—O—). Alongside these, the oxymethylene polymers contain —$(CH_2)_x$-O— units, where x can assume the values from 2 to 25. Small amounts of branching agents can be used if desired. Examples of branching agents used are alcohols whose functionality is three or higher, or their derivatives, preferably tri- to hexahydric alcohols or their derivatives. Preferred derivatives are formulas in which, respectively, two OH groups have been reacted with formaldehyde, other branching agents include monofunctional and/or polyfunctional glycidyl compounds, such as glycidyl ethers. The amount of branching agents is usually not more than 1% by weight, based on the total amount of monomer used for the preparation of the oxymethylene polymers, preferably not more than 0.3% by weight.

Oxymethylene polymers can also contain hydroxyalkylene end groups —O—$(CH_2)_x$—OH, alongside methoxy end groups, where x can assume the values from 2 to 25. These polymers can be prepared by carrying out the polymerization in the presence of diols of the general formula HO—$(CH_2)_x$—OH, where x can assume the values from 2 to 25. The polymerization in the presence of the diols leads, via chain transfer, to polymers having hydroxyalkylene end groups. The concentration of the diols in the reaction mixture depends on the percentage of the end groups intended to be present in the form of —O—(CH$_2$)$_x$—OH, and is from 10 ppm by weight to 2 percent by weight.

The molecular weights of these polymers, expressed via the volume melt index MVR, can be adjusted within a wide range. The polymers typically have repeat structural units of the formula —(CH$_2$—O—)$_n$—, where n indicates the average degree of polymerization (number average) and preferably varies in the range from 100 to 10 000, in particular from 500 to 4000.

Oxymethylene polymers can be prepared in which at least 80%, preferably at least 90%, particularly preferably at least 95%, of all of the end groups are alkyl ether groups, in particular methoxy or ethoxy groups.

Comonomers that may be used to produce oxymethylene copolymers including cyclic ethers or cyclic formals. Examples include, for instance, 1,3-dioxolane, diethylene glycol formal, 1,4-butanediol formal, ethylene oxide, propylene 1,2-oxide, butylene 1,2-oxide, butylene 1,3-oxide, 1,3 dioxane, 1,3,6-trioxocane, and the like. In general, one or more of the above comonomers may be present in an amount from about 0.1 to about 20 mol %, such as from about 0.2 to about 10 mol %, based on the amount of trioxane.

The molecular weight of the resultant homo- and copolymers can be adjusted via use of acetals of formaldehyde (chain transfer agents). These also lead to production of etherified end groups of the polymers, and a separate reaction with capping reagents can therefore be omitted. Chain transfer agents used are monomeric or oligomeric acetals of formaldehyde. Preferred chain transfer agents are compounds of the formula I $$R^1\text{—}(O\text{—}CH_2)_q\text{—}O\text{—}R^2 \qquad (I),$$

in which $R^1$ and $R^2$, independently of one another, are monovalent organic radicals, preferably alkyl radicals, such as butyl, propyl, ethyl, and in particular methyl, and q is a whole number from 1 to 50.

Particularly preferred chain transfer agents are compounds of the formula I, in which q=1, very particularly preferably methylal.

The amounts used of the chain transfer agents are usually up to 5000 ppm, preferably from 100 to 3000 ppm, based on the monomer (mixture).

The present disclosure may be better understood with reference to the following example.

Example 1

In this example, a strongly acidic ion exchange resin (Amberlyst 15®, wet form, from DOW CHEMICAL) was used as the catalyst. Before use, the resin was conditioned to sulfolane (exchange of water in the pores of the resin by sulfolane).

9 g of commercial paraformaldehyde with a water content of ca. 4 wt-% were added to 91 g of sulfolane at 145° C. with stirring. As the paraformaldehyde dissolves the temperature decreases to 122° C. The clear solution was allowed to cool to 100° C. At that temperature 10 g of Amberlyst 15® was added. After 10 min at 100° C. the reaction mixture was allowed to cool to 50° C., and no precipitate formed, indicating the conversion of the paraformaldehyde to trioxane. The concentration of the trioxane in the reaction mixture is estimated to be above 6 wt-%.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A process for producing a cyclic acetal comprising:
   combining an aqueous formaldehyde solution with an aprotic compound to form a reaction mixture, the aqueous formaldehyde solution containing formaldehyde in an amount greater than about 70% by weight;
   contacting the reaction mixture with a catalyst in a reactor under conditions that cause a portion of the formaldehyde to convert into a cyclic acetal to form a product stream, the product stream containing water, the cyclic acetal, unreacted formaldehyde, and the aprotic solvent; and
   feeding the product stream to a low pressure separating device, the low pressure separating device producing a cyclic acetal-rich gas stream and an aprotic solvent-rich liquid stream;
   quenching the cyclic acetal-rich gas stream and feeding the quenched cyclic acetal-rich stream to a distillation column for further separating the cyclic acetal from unreacted formaldehyde, the distillation column producing a cyclic acetal product stream containing the cyclic acetal, the distillation column also producing a formaldehyde-rich stream; and
   recycling the formaldehyde-rich stream and the aprotic solvent-rich stream back to the reactor.

2. A process as defined in claim 1, wherein the aqueous formaldehyde solution fed to the reactor contains formaldehyde in an amount greater than about 80% by weight.

3. A process as defined in claim 1, further comprising the step of increasing a proportionate amount of formaldehyde in the aqueous formaldehyde solution by feeding the aqueous solution through one or more concentrating devices.

4. A process as defined in claim 1, wherein the reactor comprises a fixed bed reactor, the reactor operating at a temperature of from about 30.degree. C. to about 200.degree. C. and operating at a pressure of from about 0.15 bar to about 5 bar.

5. A process as defined in claim 1, wherein the catalyst comprises an acid ion-exchange material.

6. A process as defined in claim 1, wherein the catalyst comprises an acid fixed on a solid support, the acid being a Lewis or a Broensted acid.

7. A process as defined in claim 1, where in the catalyst comprises a Lewis or Broensted acid dissolved in an organic molten salt wherein the organic molten salt can be immobilized on a solid support.

8. A process as defined in claim 1, wherein the process is continuous.

9. A process as defined in claim 1, wherein the low pressure separating device operates adiabatically, the low pressure separating device operating at a pressure of greater than about 50 mbar and less than about 600 mbar.

10. A process according to claim 1, wherein the aprotic compound has a boiling point of 140.degree. C. or higher determined at 1 bar.

11. A process according to claim 1, wherein higher than 20% of the formaldehyde source is converted into one or more cyclic acetals during the reaction.

12. A process according to claim 1, wherein the aprotic compound comprises a sulfur-containing organic compound.

13. A process according to claim 1, wherein the aprotic compound is represented by formula (I):

(I)

wherein n is an integer ranging from 1 to 6 and wherein the ring carbon atoms may optionally be substituted by one or more substituents, preferably selected from $C_1$-$C_8$-alkyl which may be branched or unbranched.

14. A process according to claim 1, wherein the aprotic compound is sulfolane.

15. A process according to claim 1, wherein the aprotic compound is represented by formula (II):

(II)

wherein $R^1$ and $R^2$ are independently selected from $C_1$-$C_8$-alkyl which may be branched or unbranched.

16. A process according to claim 1, wherein the aprotic compound is represented by formula (III):

(III)

wherein n is an integer ranging from 1 to 6 and wherein the ring carbon atoms may optionally be substituted by one or more substituents selected from $C_1$-$C_8$-alkyl which may be branched or unbranched; or the aprotic compound is represented by formula (IV):

(IV)

wherein $R^3$ and $R^4$ are independently selected from $C_1$-$C_8$-alkyl which may be branched or unbranched.

17. A process according to claim 1, wherein the aprotic compound is dimethyl sulfone.

18. A process according to claim 1, wherein the aprotic compound is dimethyl sulfoxide.

19. A process as defined in claim 1, wherein after the steps of quenching the cyclic acetal-rich gas stream and feeding the quenched cyclic acetal-rich stream to a distillation column for further separating the cyclic acetal from unreacted formaldehyde, the distillation column produces a cyclic acetal product stream containing the cyclic acetal in an amount of at least about 50% by weight.

20. A process for producing a cyclic acetal comprising:
combining an aqueous formaldehyde solution with an aprotic solvent to form a reaction mixture;
contacting the reaction mixture with a heterogeneous catalyst in a reactor under conditions that cause a portion of the formaldehyde to convert into a cyclic acetal to form a product stream, the product stream containing water, the cyclic acetal, unreacted formaldehyde, and the aprotic solvent;
feeding the product stream to a low pressure separating device, the low pressure separating device producing a cyclic acetal-rich gas stream and an aprotic solvent-rich liquid stream;
quenching the cyclic acetal-rich gas stream and feeding the quenched cyclic acetal-rich stream to a distillation column for further separating the cyclic acetal from unreacted formaldehyde, the distillation column producing a cyclic acetal product stream containing the cyclic acetal in an amount of at least about 50% by weight, the distillation column also producing a formaldehyde-rich stream; and
recycling the formaldehyde-rich stream and the aprotic solvent-rich stream back to the reactor.

* * * * *